United States Patent [19]
Carter

[11] 3,931,740

[45] *Jan. 13, 1976

[54] APPARATUS FOR COLLECTING SURFACE PARTICLE ON BODY OF WATER

[76] Inventor: Lyle Carter, 1903 33rd Ave., Oakland, Calif. 94601

[ * ] Notice: The portion of the term of this patent subsequent to May 21, 1991, has been disclaimed.

[22] Filed: Feb. 6, 1974

[21] Appl. No.: 440,171

Related U.S. Application Data

[63] Continuation-in-part of Ser. No. 302,215, Oct. 30, 1972, Pat. No. 3,811,325.

[52] U.S. Cl. .......................... 73/425.4 R; 210/242
[51] Int. Cl.² ........................................ G01N 1/12
[58] Field of Search ........... 73/421 B, 421, 425.4 R, 73/170 A; 114/235 B; 210/DIG. 21, 242

[56] References Cited
UNITED STATES PATENTS

| | | | |
|---|---|---|---|
| 3,613,629 | 10/1971 | Rhyne et al. | 114/235 B |
| 3,771,662 | 11/1973 | Muramatsu | 210/DIG. 21 |
| 3,789,988 | 2/1974 | Valibouse et al. | 210/242 |
| 3,811,325 | 5/1974 | Carter | 73/425.4 R |

Primary Examiner—S. Clement Swisher
Attorney, Agent, or Firm—Harris Zimmerman

[57] ABSTRACT

An apparatus for sampling and collecting floating particulate matter on the surface of a body of water has parallel, laterally-spaced, longitudinal tracking floats supporting a rigid tubular frame. Secured to the frame are two parallel, horizontal hydrofoil bodies spaced apart from each other to form an intake opening. A funnel-shaped net with its wide end secured to the intake opening and its narrow end terminating in a collecting screen collects surface particulate matter which is caused to flow into the intake opening as the apparatus is towed on a body of water. The lower hydrofoil body maintains the intake opening at a predetermined depth below the water surface, while the upper hydrofoil body enables the apparatus to ride over swells. In an alternative embodiment, a canvas sail is disposed above said net to form an air capturing pouch which provides a lifting force to lift and maintain the net in an attitude generally parallel to the water surface. This attitude maintenance permits the skimming of a relatively thin layer of surface water and floating matter from the bulk water below.

19 Claims, 9 Drawing Figures

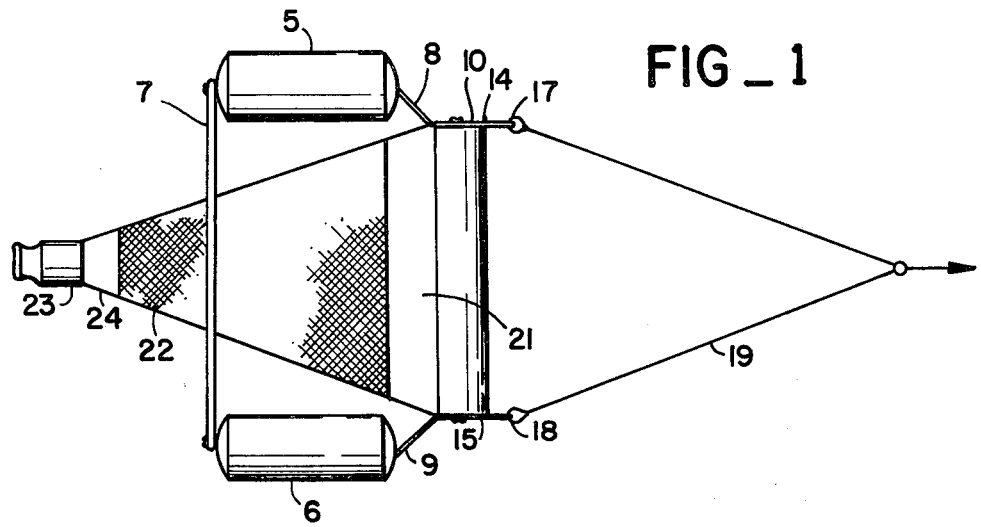
FIG_1
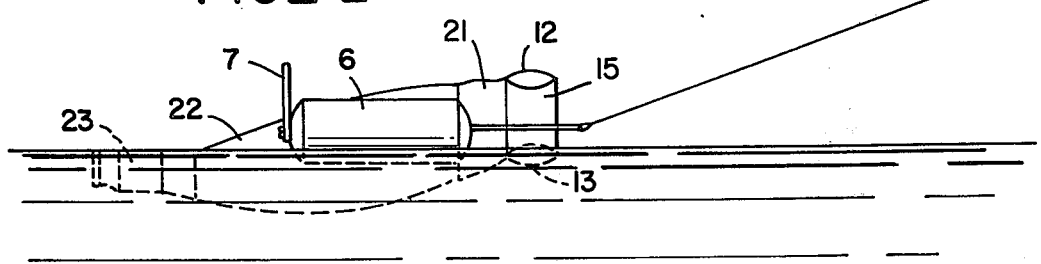
FIG_2
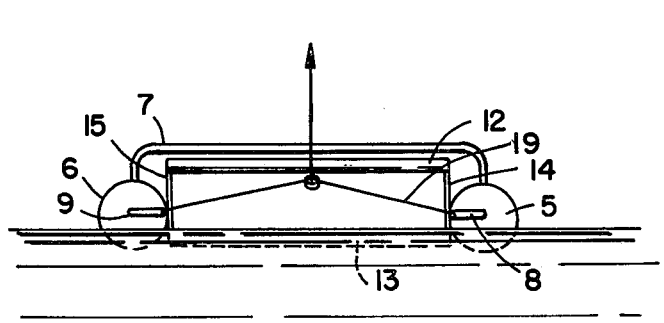
FIG_3
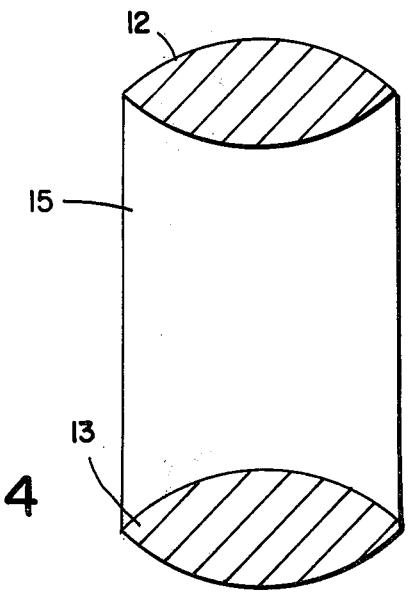
FIG_4

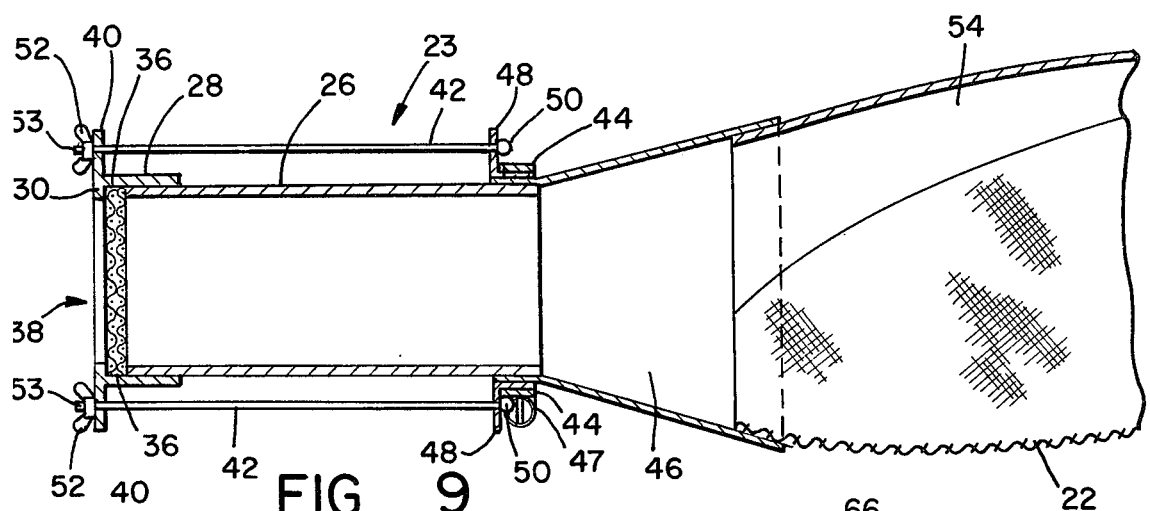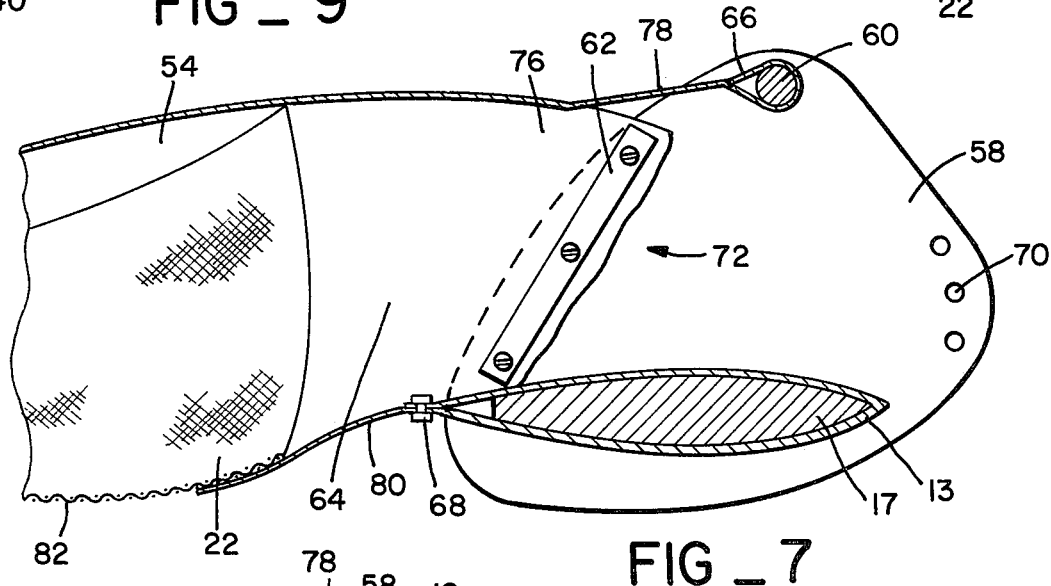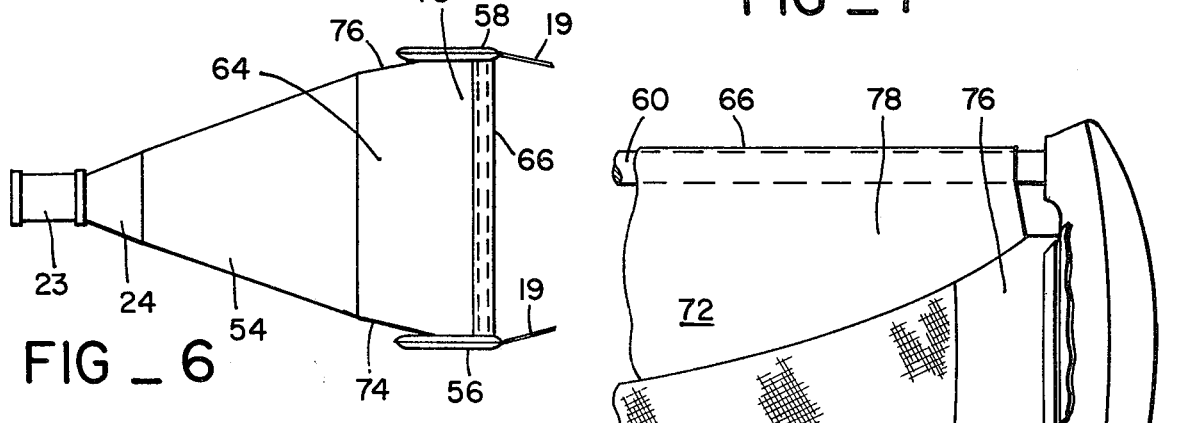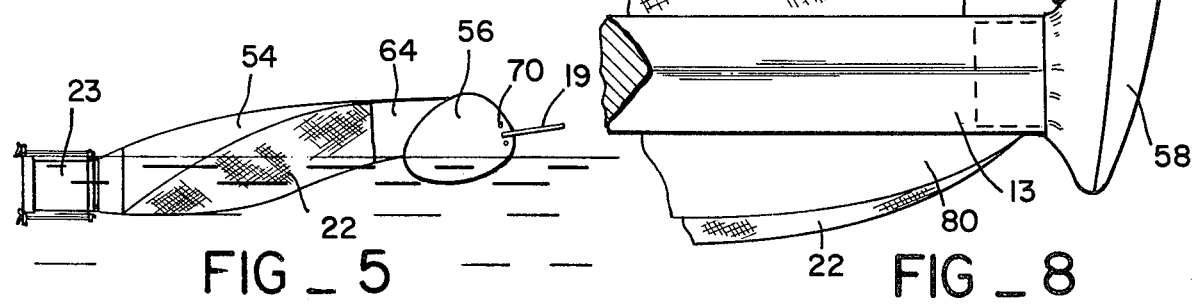

APPARATUS FOR COLLECTING SURFACE PARTICLE ON BODY OF WATER

REFERENCE TO PREVIOUS APPLICATION

This application is a continuation-in-part of my co-pending application Ser. No. 302,215, filed Oct. 30, 1972, now U.S. Pat. No. 3,811,325 for an APPARATUS FOR COLLECTING SURFACE PARTICLES ON BODY OF WATER.

BACKGROUND OF THE INVENTION

The recent interest in water quality which has been generated by the growing concern for the ecology of the earth has resulted in the surprising discovery that little is known about what constitues clean water and what compounds found in bodies of water should be labelled pollutants. Furthermore, the methods and techniques employed in sampling water to ascertain its quality vary greatly, the results varying as the method employed. One approach to ascertaining the extent and significance of surface pollution of large bodies of water is to collect and evaluate the surface floatage on the water. This floatage may include substances varying in size from large floating particulates such as feathers and insects to fine microparticulates, bacteria, surface plankton, and surface-active molecules. Prior art devices, which are generally oriented toward removing oil slicks or collecting other specific floatage, cannot collect all of the floatage in the described range of size. Further, much of the surface floatage material has the property of sinking mementarily when encountering any water turbulence. Thus, an effective sampler of surface floatage must skim the surface water without creating any leading turbulence. Prior art devices avoid this problem by scooping the water below the surface as well to ensure catching any sinking floatage. These devices, however, collect submerged as well as surface floatage.

SUMMARY OF THE INVENTION

The present invention is directed toward a water quality sampling device for collecting surface floatage on a body of water. the sampling device which is towed on the surface of the water is supported by two parallel, laterally-spaced tracking floats. Secured between said floats is a rigid tubular framework with two horizontal hydrofoil bodies transverse to the floats secured to the framework within the profile of the floats. The vertically stacked hydrofoil bodies defined an intake opening, with the lower hydrofoil maintaining the intake opening at a predetermined depth below the water without causing disruptive turbulence, while the upper hydrofoil causes the sampling device to ride over swells and waves. The towing motion causes surface water to flow into the intake opening, where the surface floatage is collecting by a funnel-shaped net which has its wide end secured to the intake opening. The net, with the narrow end terminated by a collecting screen, lies partially submerged between the floats.

THE DRAWINGS

FIG. 1 is a plan view of the present invention;

FIG. 2 is a side view of an embodiment of the present invention;

FIG. 3 is a front end view of the present invention;

FIG. 4 is a detail side view of the present invention;

FIG. 5 is a side view of an alternative embodiment of the present invention;

FIG. 6 is a plan view of the alternative embodiment of FIG. 5;

FIG. 7 is a side view of the alternative embodiment of FIG. 5;

FIG. 8 is a front end view of the alternative embodiment of FIG. 5;

FIG. 9 is a detail side sectional view of the screen sampler portion of the alternative embodiment of FIG. 5.

DESCRIPTION OF THE PREFERRED EMBODIMENT

As shown in FIG. 1, the present invention includes two substantially-cylindrical, parallel tracking floats 5 and 6 fabricated of metal, fibreglas, or the like. The floats are each secured at one end to the arched rear tubular frame member 7, and at the other end to fixed arms 8 and 9, thus rigidly maintaining the floats in a fixed spaced-apart relationship. The arms 8 and 9 are secured to the rectangular intake opening 10. The intake opening is formed by hydrofoil bodies 12 and 13 and vertical panels 14 and 15, shown in FIG. 3. Protruding forward of the intake opening are towing eyes 17 and 18, to which a towing bridle 19 is secured. A fabric collar 21 of canvas or similar material attached to the intake opening secures the collecting travel net 22 to the intake. The collecting net, which is typically fabricated of nylon or fibreglass cloth, allows water from the intake to pass through its 500 $\mu$ pore mesh, while capturing any particulates larger than that size. The narrow end of the travel net is closed by a screen sampler 23 secured to the net by collar 24. The screen sampler is a fine mesh cloth of inert material such as fibreglas or nylon, which captures fine microsize particulates and organisms. The travel collecting net and the screen sampler cooperate to trap all large particulate floatage within the net, while the collating screen prevents any microparticulates from escaping collecting.

In use the present invention is towed from the boom of a boat in a predetermined direction in the undisturbed water adjacent said boat. The tracking floats stabilize the intake opening against yaw action, and serve a rudder function in maintaining the towed assembly oriented in said predetermined direction. The velocity of the towing boat is monitored and, together with data concerning the length of time of a sampling run and the width of the intake opening, the area covered by a sampling run can be determined. A typical embodiment of the present invention may have an intake opening approximately 1.0 meter wide, and is towed at a velocity of approximately 1.5 knots. After a sampling run is made, the screen sampler 33 is removed and stored for laboratory analysis, a new screen is inserted, and the surface water quality sampling device is ready for another run.

As shown in FIG. 2, the travel net lies partially submerged between the floats, while the screen sampler is completely submerged to ensure that the collected floatage remains in its natural state. The hydrofoil body 13, which rides just below the surface of the water, is shaped to prevent any bow wave turbulence which might cause the surface floatage to sink. Also, the body 13 may be adjusted to control the depth of water sampled, typically from a minimum depth of 2 mm. to a maximum of 2 cm. As shown in FIG. 4, the body 13 skims just below the water surface, directing the surface floatage into the intake opening while avoiding any suspended particulate matter. The upper hydrofoil body 12, shown in FIG. 4, is spaced above body 13 by approximately 20 cm. It is designed to ride up and over any swells or waves, preventing any damage both to the sampling device and to the collected floatage within.

It should be noted that although the lower hydrofoil body is necessary to control sampling of a minimum depth of surface water, the upper hydrofoil body may not be necessary in embodiments of the present invention which are intended for use only in calm water conditions.

While the aforediscussed embodiment performs its collecting function well in extremely calm sea conditions at very low trawling speeds, difficulties are encountered in stabilizing the net in slightly turbulent sea conditions and at slightly higher trawling speeds because the floats tend to cause the entire leading surface of the apparatus to "porpoise," i.e., alternately to dive below and rise above the water surface. To overcome this drawback, an alternative embodiment is illustrated in FIGS. 5 through 9. This alternative embodiment is particularly well suited to sample a relatively broad surface area of water in a relatively thin but constant layer of the water surface.

As is best seen in FIGS. 5 and 6, the major elements of the instant apparatus are retained, i.e, screen sampler 23, net 24 and lower hydrofoil body 13 are retained. However, the two external floats, the float frame, and the upper hydrofoil body are eliminated; a top canvas strip 54 is provided to mechanically connect the net 24 to the upper hydrofoil body 12; and two side vertical tracking foils 56 and 58 are added, said foils being connected by a transverse support rod 60.

Details of these components of this alternative embodiment are best seen in FIGS. 7 and 8. Lower hydrofoil 13 is provided with a cavity therein, wherein is disposed a low-density solid material 17 to provide a buoyant effect when submerged. This bouyant effect prevents the entire apparatus from sinking when first placed into the water and when dead in the water under no traveling headway. And, as may be appreciated from FIG. 5, this bouyant effect, coupled with the downward drag of the net 22, causes the leading edge of the hydrofoil body 13 to be placed in a slightly upward attitude so that said hydrofoil body immediately begins to rise in the water when the slightest trawing headway is applied. Each of the side vertical foils 56 and 58 is provided with a plurality of towing eyes 70 to which the towing bridle 19 may be attached. Thus, by considered selection of particular towing eyes, the angle of attack of the hydrofoil body 13 can be varied for differing sampling depths and trawling speeds.

The net 22 is secured to a canvas sail 54 which is disposed generally above said net, and which itself is attached to a multiflapped canvas skirt 64 whose two side flaps 74 and 76 are secured to vertical foils 56 and 58, respectively; whose top flap 78 is secured by clamps 62 to transverse support rod 60 by a sewn loop 66; and whose bottom flap 80 is secured to hydrofoil body 13 by rivets 68. The aft portions of both net 22 and sail 54 are secured by stitching to a funnellike canvas collar 46 which is itself secured to the screen sampler 23, as discussed below. Thus, as may be appreciated from FIGS. 7 and 8, when so secured, skirt 64 forms with sail 54 and net 22 a pouchlike envelope 72. Hence, when the apparatus is trawled, envelope 72 will scoop and capture passing air, this action providing a lifting force to lift the net 22 and screen sampler 23 and hold both in an attitude generally parallel to the water surface, as shown in FIG. 6. This attitude then permits skimming of a relatively thin layer of surface water and floating matter from the bulk water below.

The detail of the screen sampler 23 of this alternative embodiment is best seen in FIG. 9. The basic structural member of sampler 23 is a generally cylindrical barrel member 26 whose major cylindrical axis lies parallel to the direction of water flow through said sampler. Affixed to the aft terminal extremity of barrel member 26 is a generally cylindrical retaining ring 28 with a circular retaining flange 30. Generally normally disposed to the flow of water within barrel member 26 is a generally rigid coarse-mesh backing screen 32, and a collector screen 34 comprising the aforediscussed fine-mesh cloth. The collector screen 34 is supported by said backing screen 32, said collector screen 34 also being disposed generally normally to the flow of water within barrel member 26. Backing screen 32 is retained in place within barrel member 26 by being compressively engaged with annular gasket 36 which forms a watertight barrier at the point of engagement. Thus, it may be seen that water flowing within barrel member 26 from fore to aft (i.e., from left to right in FIG. 5), must pass through the apertures in both screens 32 and 34 and exhaust via generally circular opening 38 in barrel member 26.

Retaining ring 28 is retained in position with respect to barrel member 26 in the following fashion. Spaced about the outer periphery of the aft extremity of ring 28 and attached thereto are a plurality of lugs 40, each said lug having a bore hole therein for the passage of cable 42. Encircling the forward extremity of barrel member 26 is a circular clamp 44, of the type generally known as a hose clamp, provided with an adjustment screw 47 for tightening or loosening said clamp. As is seen in FIG. 9, the funnel-like canvas collar 46 which, as previously discussed, is stitched to both net 22 and canvas sail 54, is inserted between said clamp and said barrel-member outer periphery. Said clamp is then tightened by said screw 47 thereby securing said clamp in stationary fashion with respect to said barrel member. Spaced about the periphery of clamp 44 and attached thereto are a plurality of lugs 48, each said lug having a bore hole therein for the passage of cables 42. Thus it may be seen that, when terminal beads 50 affixed to cables 42 are drawn up snuggly against lugs 48 by tightening wing nuts 52 on threaded portions 53 of said cables adjacent lugs 40, retaining ring 28 is compressed into stationary position with respect to barrel member 26. And, as is also seen FIG. 9, compression of said ring serves to lock the backing screen 32 into place against gasket 36.

It may be appreciated that many additional embodiments are conceivable within the scope of the present invention. For example, if it is desired to take water samples in extremely turbulent seas, the transverse support rod may be replaced with an upper hydrofoil to provide additional lift when the apparatus is forced under the water surface by large waves. Further, this upper hydrofoil body may be positioned so that its leading edge extends forward beyond the leading edge of lower hydrofoil body 13, so as to capture surface water and floating matter which are thrown upwardly by the lower hydrofoil body in turbulent seas. And, should additional rigidity of the net be desired, a canvas sheet can be disposed subjacent said net between the rivets 68 on lower hydrofoil body 13 and the canvas collar 46.

Thus it may be seen that the present invention provides a unique means and method for sampling and collecting surface floatage. Moreover, the present invention provides a long-sought means of standardizing the sampling of surface water quality, thereby allowing tests of water quality conducted at different times and locations to be analyzed and compared productively.

I claim:

1. A water-quality sampling device for collecting surface floatage from a body of water comprising:
   towing means for moving said device on said body of water in a predetermined direction;
   laterally-spaced tracking means for maintaining said device in alignment in said predetermined direction; and
   collecting means for removing said surface floatage from said surface water, said collecting means comprising intake opening means opening toward said predetermined direction for receiving oncoming surface water and a net having a forward opening extending for substantially the width of said device and disposed between said tracking means and having a smaller rear opening terminating in a sampler means, said sampler means being disposed rearwardly of said tracking means.

2. The device of claim 1 further comprising a first hydrofoil means secured to said intake opening means for controlling the depth of surface water received by said intake opening means.

3. The device of claim 1 wherein said forward opening is secured to said intake opening means, said intake opening means directing said oncoming surface water into said forward end of said net.

4. The device of claim 1 wherein said sampler means comprises at least one fine-mesh collector screen.

5. The device of claim 1 wherein said tracking means comprises buoyancy means for maintaining said device on the surface of said body of water.

6. The device of claim 5 wherein said buoyancy means comprises elongated float means with longitudinal axes aligned parallel to said predetermined direction.

7. The device of claim 6 wherein said float means comprises two laterally-spaced elongated floats secured to rigid frame means to maintain said floats in a spaced relationship generally normal to said predetermined direction of travel.

8. The device of claim 6 wherein said intake opening means is generally normal to said floats and secured therebetween and directs said oncoming surface water into said net front opening.

9. The device of claim 2 further comprising second hydrofoil means secured generally above and spaced from said first hydrofoil means to ride up and over any turbulence in said oncoming water.

10. The device of claim 9 wherein a leading edge of said second hydrofoil extends beyond the leading edge of said first hydrofoil in said predetermined direction.

11. The device of claim 1 wherein said tracking means comprises laterally-spaced vertical foils with longitudinal axes parallel to said predetermined direction.

12. The device of claim 1 further comprising buoyancy means for maintaining said device on the surface of said body of water.

13. The device of claim 12 wherein said buoyancy means comprises a hollow hydrofoil means having a low-density material contained therein.

14. The device of claim 11 further including a hydrofoil means disposed between said foils, the longitudinal axis of said hydrofoil means being generally normal to said predetermined direction.

15. The device of claim 1 further comprising a sail means disposed generally above said net.

16. The device of claim 15 wherein a leading distal extremity of said sail means is disposed generally adjacent and above said intake opening means.

17. The device of claim 15 wherein a rearward distal extremity of said sail means is disposed generally adjacent and forward of said sampler means, and operatively connected thereto.

18. The device of claim 15 wherein an air-capturing pouch is formed between said sail means and an upper surface of said net.

19. The device of claim 4 wherein said sampler means further comprises a generally-cylindrical barrel member whose major cylindrical axis lies parallel to said predetermined direction, and a coarse-mesh backing screen, the major axes of said backing screen and said collector screen being disposed generally normal to said predetermined direction.

* * * * *